(12) United States Patent
Clarke

(10) Patent No.: US 12,049,351 B2
(45) Date of Patent: Jul. 30, 2024

(54) SYSTEM AND METHOD FOR DISPENSING TABLETS

(71) Applicant: UMF Corporation, Skokie, IL (US)

(72) Inventor: George Clarke, Skokie, IL (US)

(73) Assignee: UMF Corporation, Northbrook, IL (US)

(*) Notice: Subject to any disclaimer, the term of this patent is extended or adjusted under 35 U.S.C. 154(b) by 0 days.

(21) Appl. No.: 17/836,343

(22) Filed: Jun. 9, 2022

(65) Prior Publication Data

US 2023/0399165 A1 Dec. 14, 2023

(51) Int. Cl.
 B65D 83/04 (2006.01)
(52) U.S. Cl.
 CPC .... *B65D 83/049* (2013.01); *B65D 2583/0431* (2013.01); *B65D 2583/0481* (2013.01)
(58) Field of Classification Search
 CPC ....... A61J 1/03; B65D 83/0038; B65D 83/04; B65D 83/049; B65D 83/0409; B65D 83/0418; B65D 2583/005; B65D 2583/04; B65D 2583/0431; B65D 2583/0454; B65D 2583/0468; B65D 2583/0481
 See application file for complete search history.

(56) References Cited

U.S. PATENT DOCUMENTS

| | | | | |
|---|---|---|---|---|
| 2,567,089 A * | 9/1951 | Walsh | ............... | B65D 83/0409 221/246 |
| 2,683,554 A * | 7/1954 | Mulhauser, Jr. | ... | B65D 83/0409 221/152 |
| 3,602,393 A * | 8/1971 | Hughes | ................... | A47F 1/085 221/283 |
| 3,854,626 A * | 12/1974 | Krechmar | .......... | B65D 83/0418 221/273 |
| 4,415,098 A * | 11/1983 | Haas | ................... | B65D 83/0409 221/202 |
| 4,531,658 A * | 7/1985 | Galopin | .................. | G01F 11/18 222/361 |
| 4,752,807 A * | 6/1988 | Mort | ..................... | G03G 15/087 141/346 |
| 6,273,315 B1 * | 8/2001 | McGuinness | ......... | B25C 5/1693 227/138 |
| 6,450,371 B1 * | 9/2002 | Sherman | ................. | G01F 11/18 222/336 |
| 6,805,262 B1 * | 10/2004 | Frazier | ................. | A47K 5/1214 221/96 |
| 9,505,544 B2 * | 11/2016 | Leifeld | .............. | B65D 83/0418 |
| 10,643,410 B2 * | 5/2020 | Kho | ................... | G07C 9/00309 |
| 11,383,922 B2 * | 7/2022 | Lee | .......................... | D06F 39/02 |

* cited by examiner

*Primary Examiner* — Gene O Crawford
*Assistant Examiner* — Kelvin L Randall, Jr.
(74) *Attorney, Agent, or Firm* — Flener IP & Business Law; Zareefa B. Flener

(57) ABSTRACT

A tablet dispensing system comprises a sleeve having a first opening at a first end and a second opening at a second end, a base attached to the second end, the base including a first barrier disposed transversely to and a predetermined distance from the second opening, and a slide having second and third barriers separated by a riser, wherein the second and third barriers include aligned passages disposed therethrough. The slide is disposed on the base so that the first barrier is positioned between the second and third barriers and the slide is biased by a spring toward a first side of the sleeve so that the first barrier blocks at least one of the aligned passages, where the spring is disposed between the base and the slide.

15 Claims, 17 Drawing Sheets

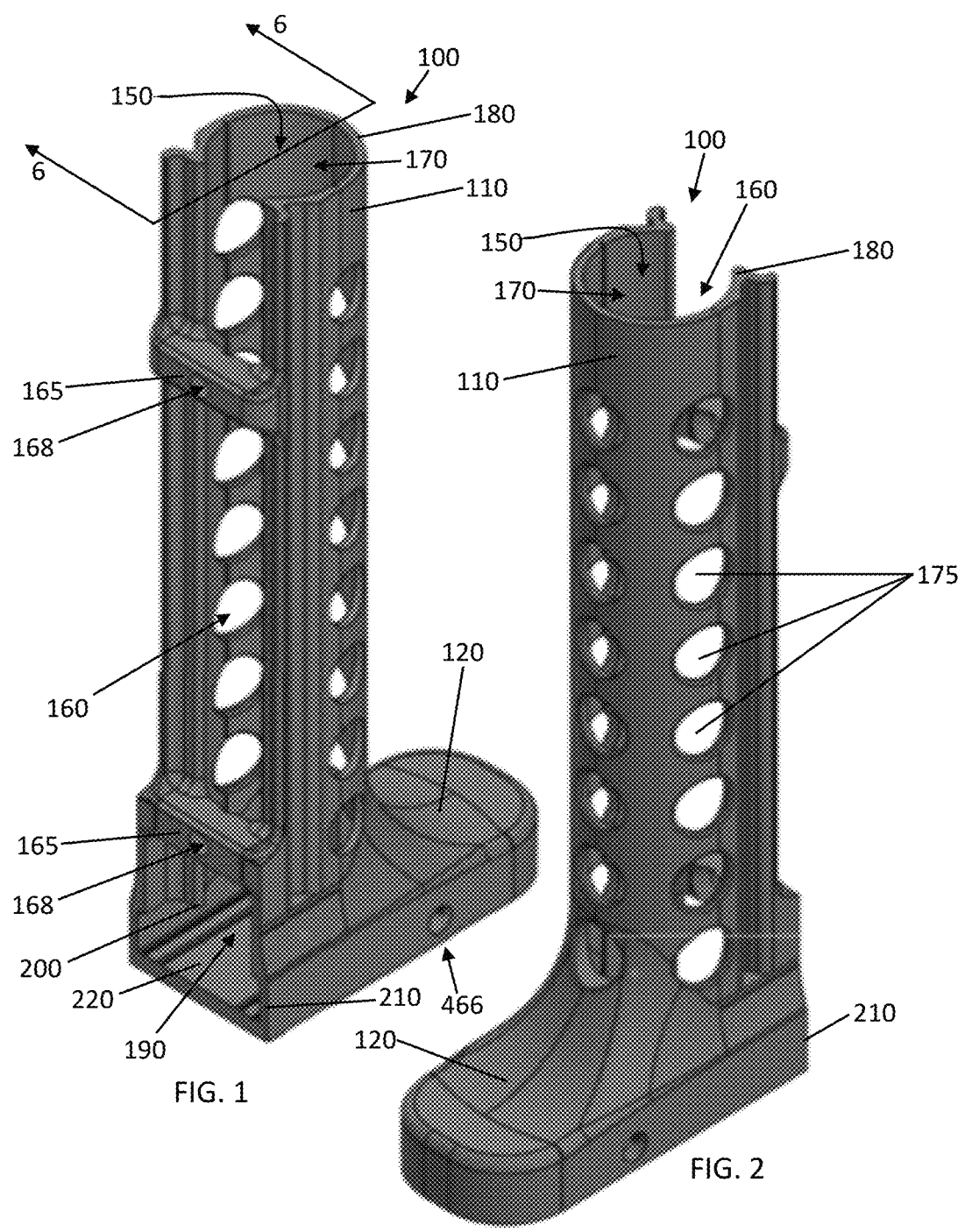

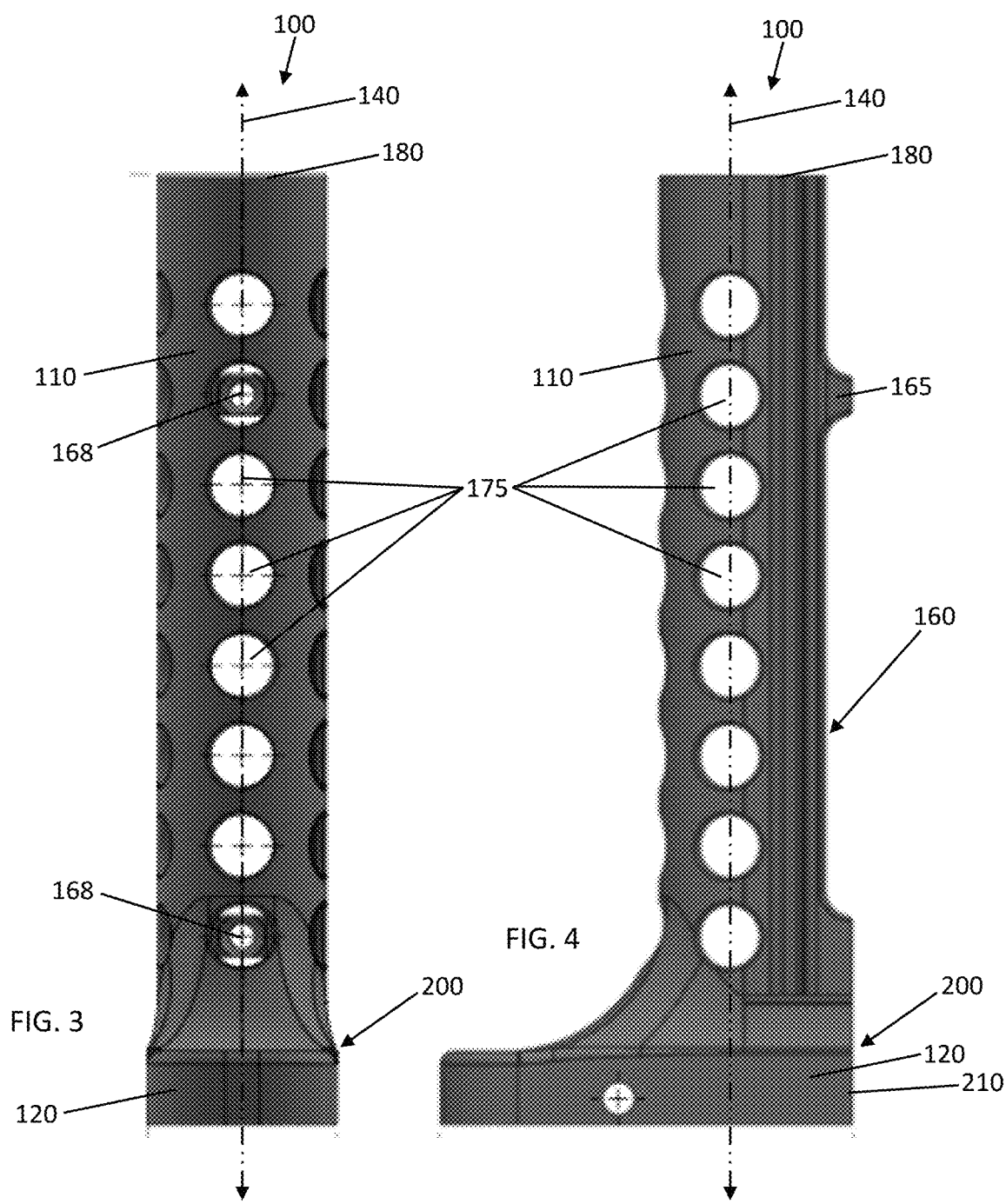

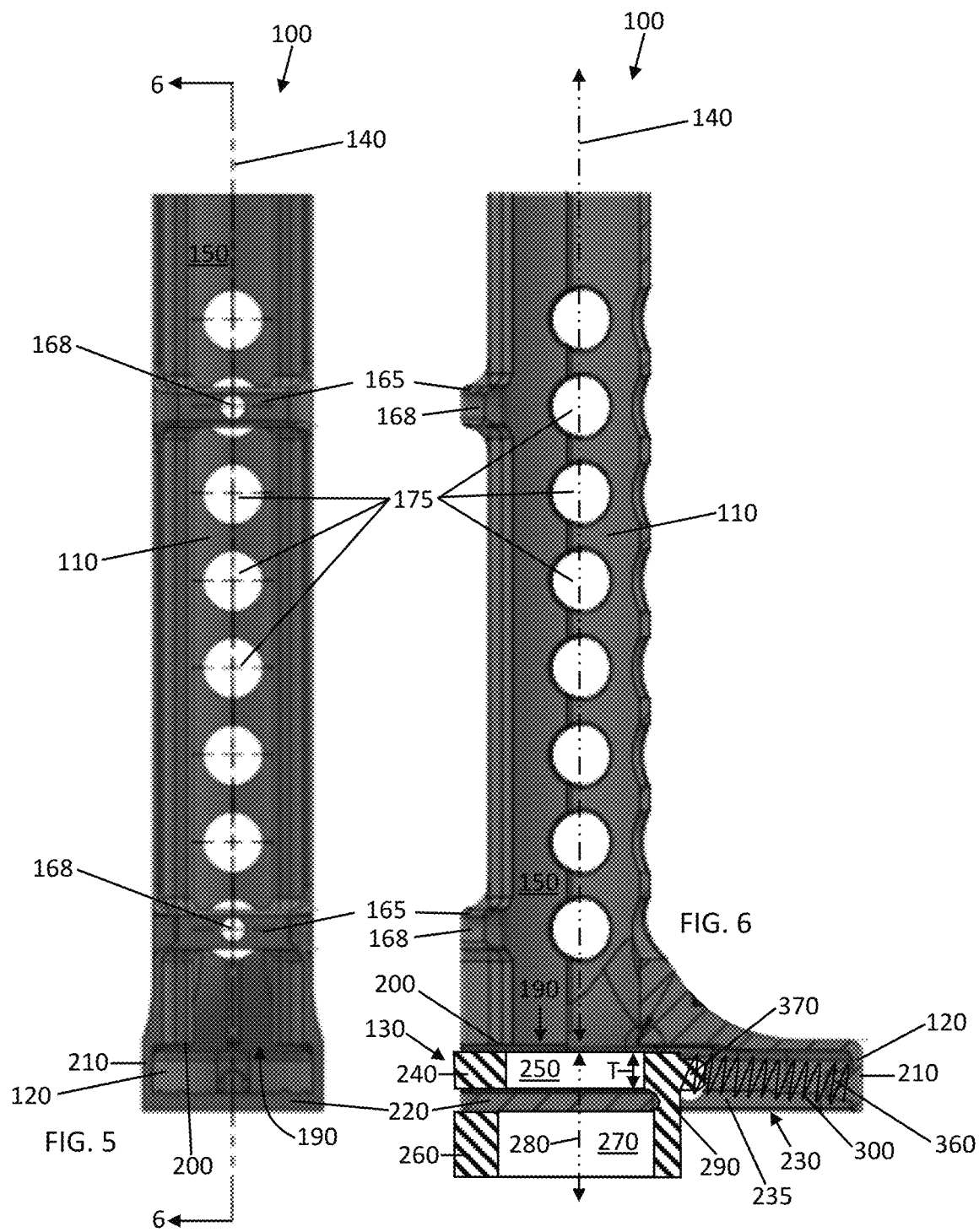

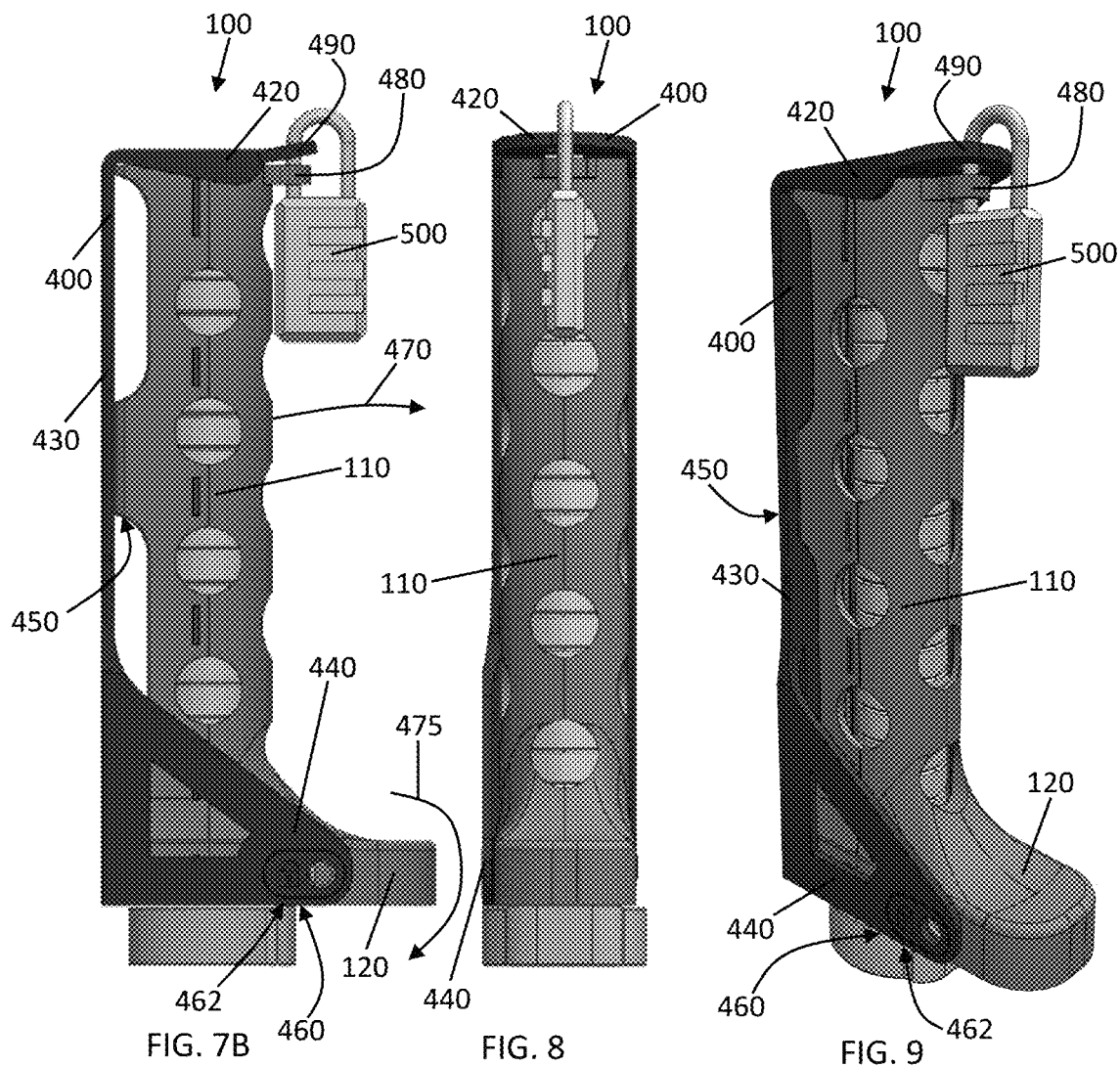

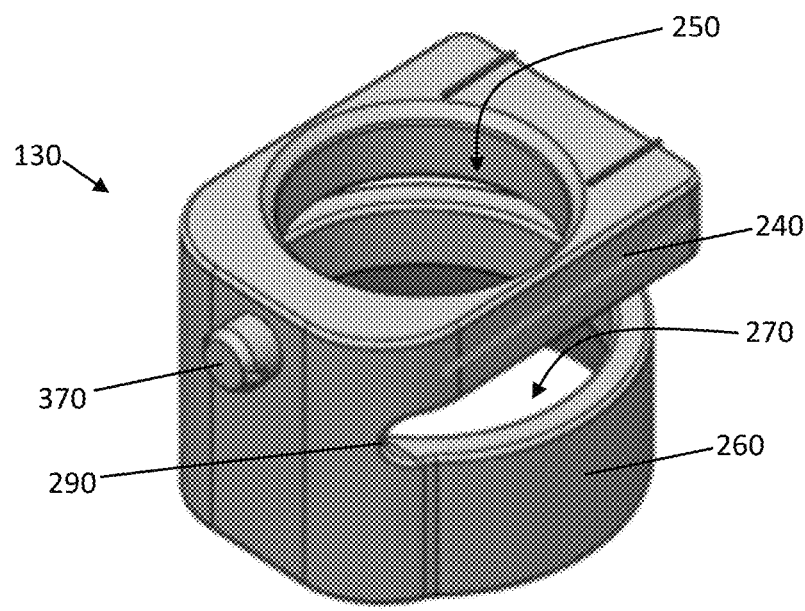
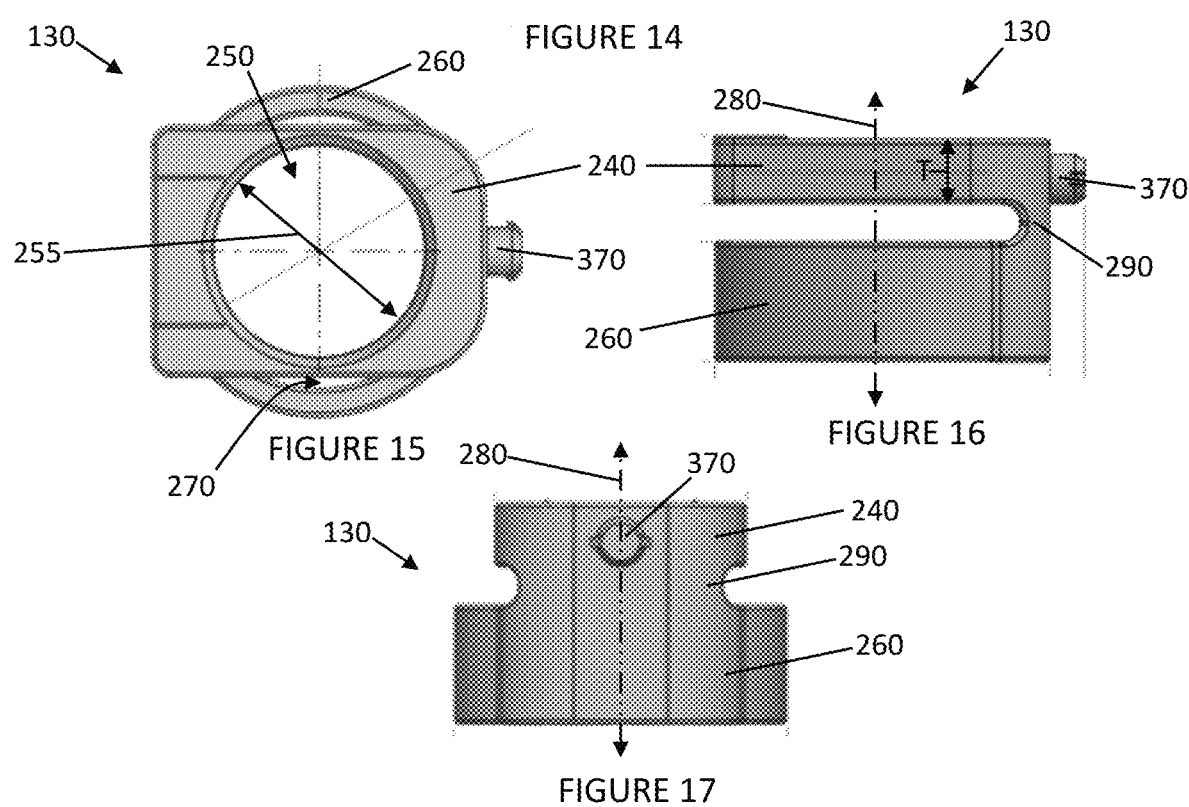

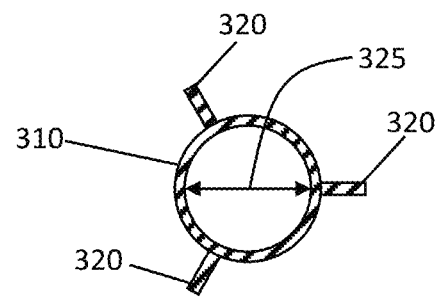
FIGURE 18A
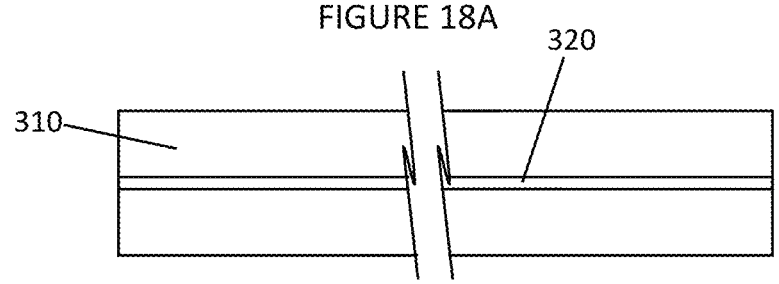
FIGURE 18B
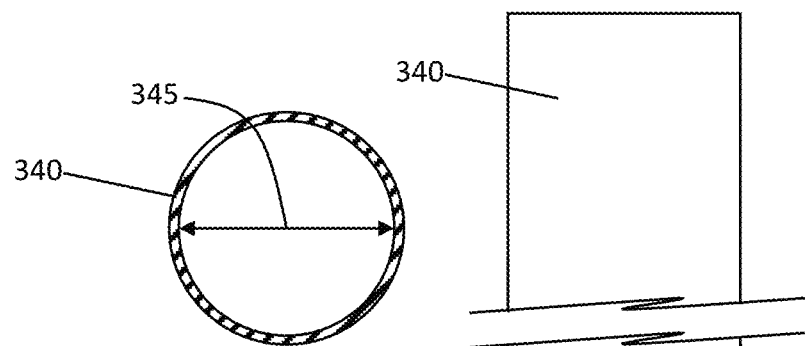
FIGURE 19A
FIGURE 19B

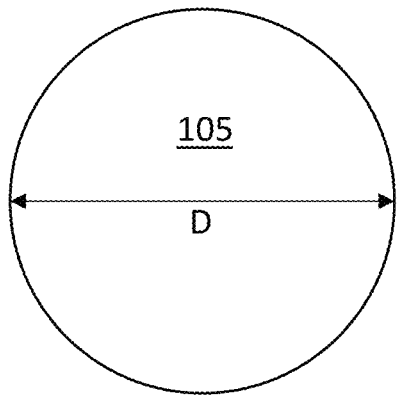
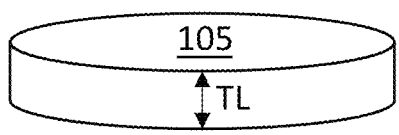
FIGURE 25
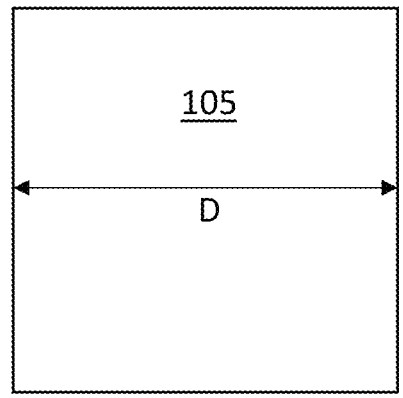
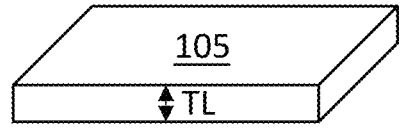
FIGURE 26
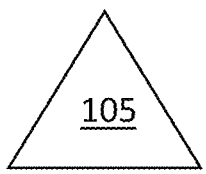
FIGURE 27
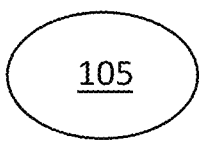
FIGURE 28
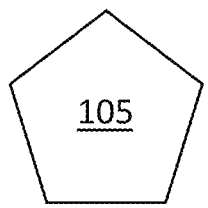
FIGURE 29
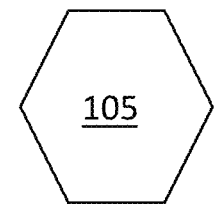
FIGURE 30

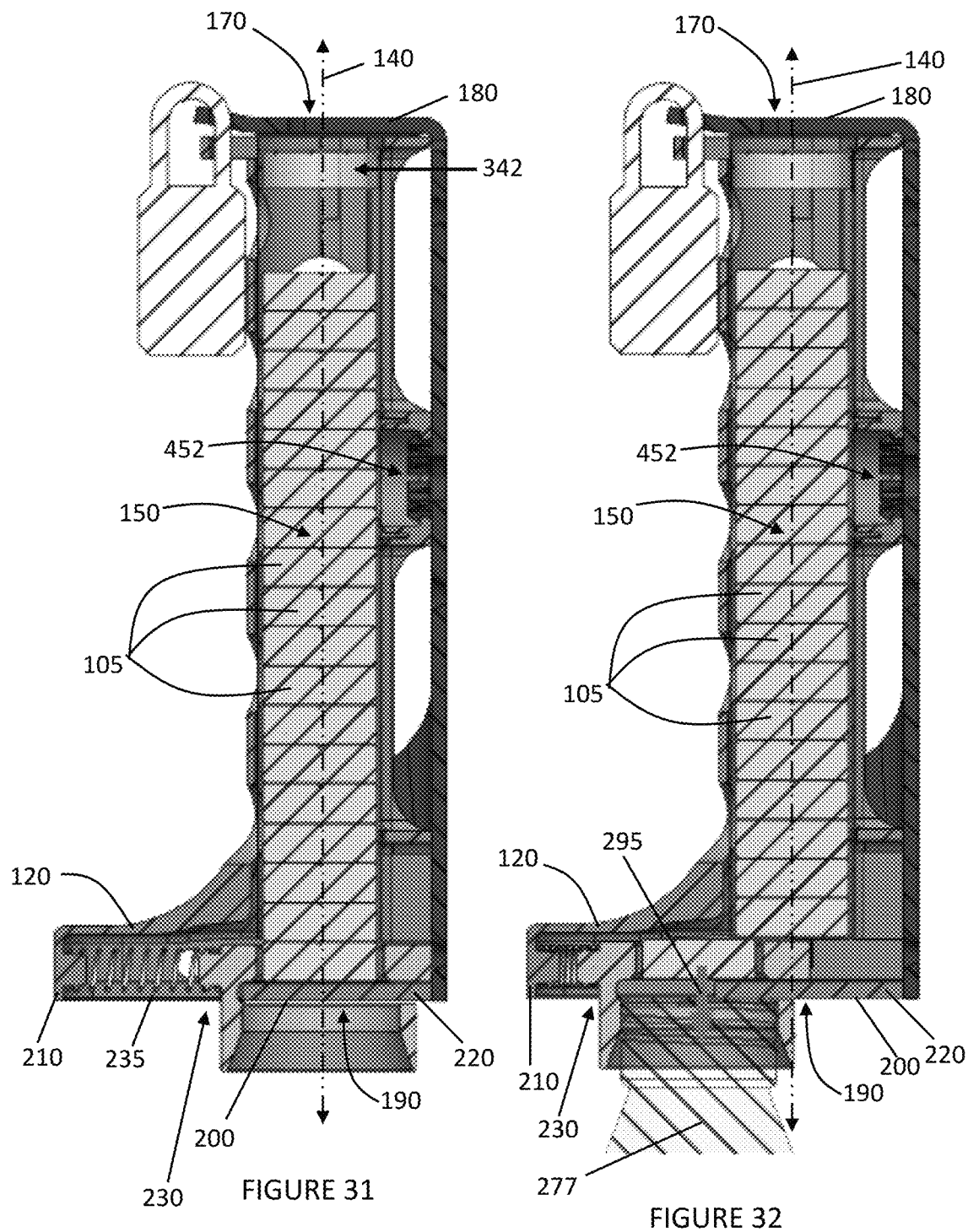

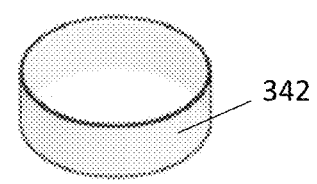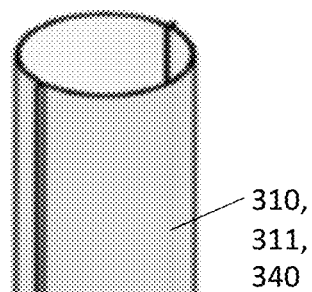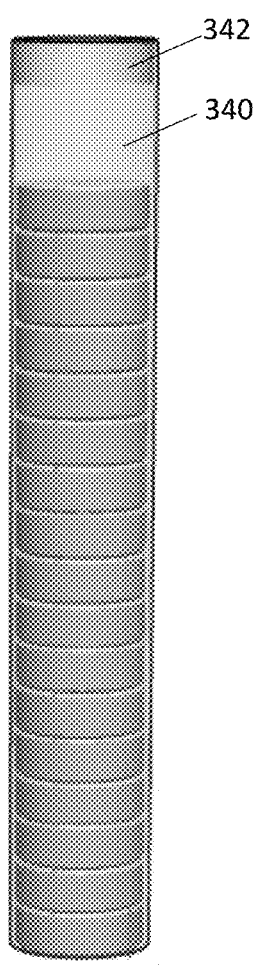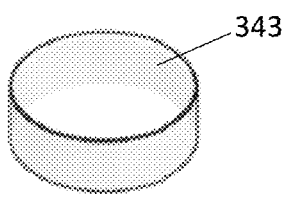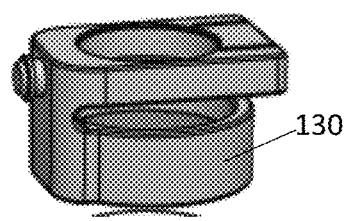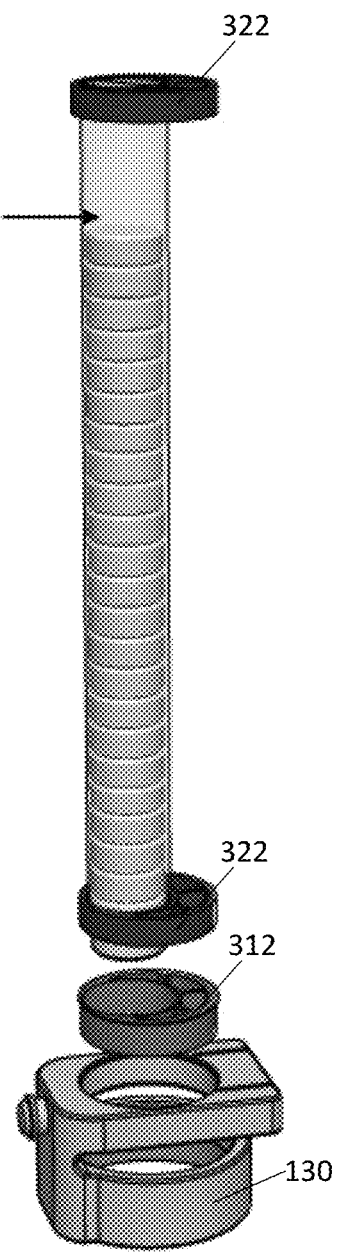
FIGURE 33            FIGURE 34            FIGURE 35

SYSTEM AND METHOD FOR DISPENSING TABLETS

FIELD OF THE INVENTION

The present invention relates to a tablet dispensing system. More specifically, the present invention relates to a tablet dispensing system that controllably dispenses one tablet at a time while accommodating tablets of different sizes.

BACKGROUND

Disinfectant tablets are often used in preparation of solutions for wiping down surfaces to prevent the spread of disease by contact. Tablets are typically mixed with water or other solutions containing water and sprayed or wiped onto the surface to be cleaned. In recent years the form of disinfectant tablets used in the creation of the cleaning solutions has been standardized with requirements regarding tablet size and/or the mode of distribution. For example, one exemplary requirement to help prevent the spread of disease and maintain the efficacy of the tablets is that the tablets being dispensed cannot be touched by human hands.

In some countries the standardization has gone further to include the size of the disinfectant tablets. So there exists a need for a tablet dispensing system to dispense disinfectant tablets of a particular size (or sizes) into a solution without being touched. It would be helpful if such a tablet dispensing system could be mounted on a wall or utility cart and dispense the tablets, one at a time, directly into a bottle, pail, or container. It would be further helpful if such a tablet dispensing system could be locked in place once loaded with tablets to prevent unauthorized use, tampering with, or theft of the tablets. Such a tablet dispensing system also being able to accommodate tablets of differing sizes with only a minor change in components or an adapter would be especially useful.

SUMMARY OF THE INVENTION

According to one aspect of the invention, a tablet dispensing system comprises a sleeve defining a first longitudinal axis and having a first opening at a first end and a second opening at a second end, a base extending transversely from the second end, and a peripheral skirt extending longitudinally from the base. A transversely extending first barrier is supported by the peripheral skirt at a predetermined distance from the second end and intersecting with the first longitudinal axis of the sleeve. The tablet dispensing system further comprises a slide having a second longitudinal axis, a first transversely extending level having a first passage disposed therethrough and a second transversely extending level having a second passage disposed therethrough, wherein the first and second levels are separated longitudinally by a riser, and a spring. The slide is disposed with the first level between the first barrier and the second end and transversely biased by the spring so that the first and second longitudinal axes are aligned, wherein the spring is disposed between the peripheral skirt and the slide.

According to another aspect of the invention, a tablet dispensing system comprises a sleeve having a first opening at a first end and a second opening at a second end, a base attached to the second end, the base including a first barrier disposed transversely to and a predetermined distance from the second opening, and a slide having second and third barriers separated by a riser, wherein the second and third barriers include aligned passages disposed therethrough. The slide is disposed on the base so that the first barrier is positioned between the second and third barriers and the slide is biased by a spring toward a first side of the sleeve so that the first barrier blocks at least one of the aligned passages, where the spring is disposed between the base and the slide.

BRIEF DESCRIPTION OF THE DRAWINGS

FIG. 1 is a rear perspective view of an exemplary sleeve according to an embodiment;

FIG. 2 is a front perspective view of the exemplary sleeve shown in FIG. 1;

FIG. 3 is a front elevational view of the exemplary sleeve shown in FIG. 1;

FIG. 4 is a left side view of the exemplary sleeve shown in FIG. 1;

FIG. 5 is a rear elevational view of the exemplary sleeve shown in FIG. 1;

FIG. 6 is a cross-sectional view of the exemplary sleeve shown in FIG. 1 taken generally along the lines 6-6 in FIG. 1 and further including an exemplary slide according to an embodiment;

FIG. 7B is a right side view of an exemplary dispensing system according to an embodiment;

FIG. 8 is a front elevational view of the exemplary dispensing system shown in FIG. 7;

FIG. 9 is a front perspective view of the exemplary dispensing system shown in FIG. 7;

FIG. 14 is a front perspective view of a first embodiment of a slide;

FIG. 15 is a top plan view of the slide shown in FIG. 14;

FIG. 16 is a right side view of the slide shown in FIG. 14;

FIG. 17 is a front elevational view of the slide shown in FIG. 14;

FIG. 18A is a top plan view of a first embodiment of a tube adapter;

FIG. 18B is a side view of the tube adapter shown in FIG. 18A;

FIG. 19A is a top plan view of a second embodiment of a tube adapter;

FIG. 19B is a side view of the tube adapter shown in FIG. 19A;

FIG. 25 illustrates an exemplary tablet that can be used with the tablet dispensing system according to an embodiment;

FIG. 26 illustrates an exemplary tablet that can be used with the tablet dispensing system according to another embodiment;

FIG. 27 illustrates a top plan view of an exemplary tablet that can be used with the tablet dispensing system according to a further embodiment;

FIG. 28 illustrates a top plan view of an exemplary tablet that can be used with the tablet dispensing system according to yet another embodiment;

FIG. 29 illustrates a top plan view of an exemplary tablet that can be used with the tablet dispensing system according to yet a further embodiment;

FIG. 30 illustrates a top plan view of an exemplary tablet that can be used with the tablet dispensing system according to a still further embodiment;

FIG. 31 is a cross-sectional view of an exemplary tablet dispensing system in a ready to dispense configuration taken generally along the lines 31-31 of FIG. 13B according to an embodiment;

FIG. 32 is a cross-sectional view of an exemplary tablet dispensing system in a dispensing configuration taken generally along the lines 31-31 of FIG. 13B according to an embodiment;

FIG. 33 shows a tube adapter having insert plugs for disposal in both ends thereof according to an embodiment;

FIG. 34 illustrates an exemplary tube adapter and slide combination according to an embodiment; and FIG. 35 illustrates an exemplary tube adapter and slide combination according to another embodiment.

Other aspects and advantages of the present invention will become apparent upon consideration of the following detailed description, wherein similar structures have similar reference numerals.

DETAILED DESCRIPTION

The following detailed embodiments presented herein are for illustrative purposes. That is, these detailed embodiments are intended to be exemplary of the present invention for the purposes of providing and aiding a person skilled in the pertinent art to readily understand how to make and use of the present invention. Material used herein include, for example without limitation, plastics including without limitation plastics made from and/or coated with anti-microbial materials. Any other suitable materials as known in the art may also be used. Methods for making the components of the present invention include, for example without limitation, injection molding and/or any other suitable methods for manufacturing as are known in the art.

Figure 10:
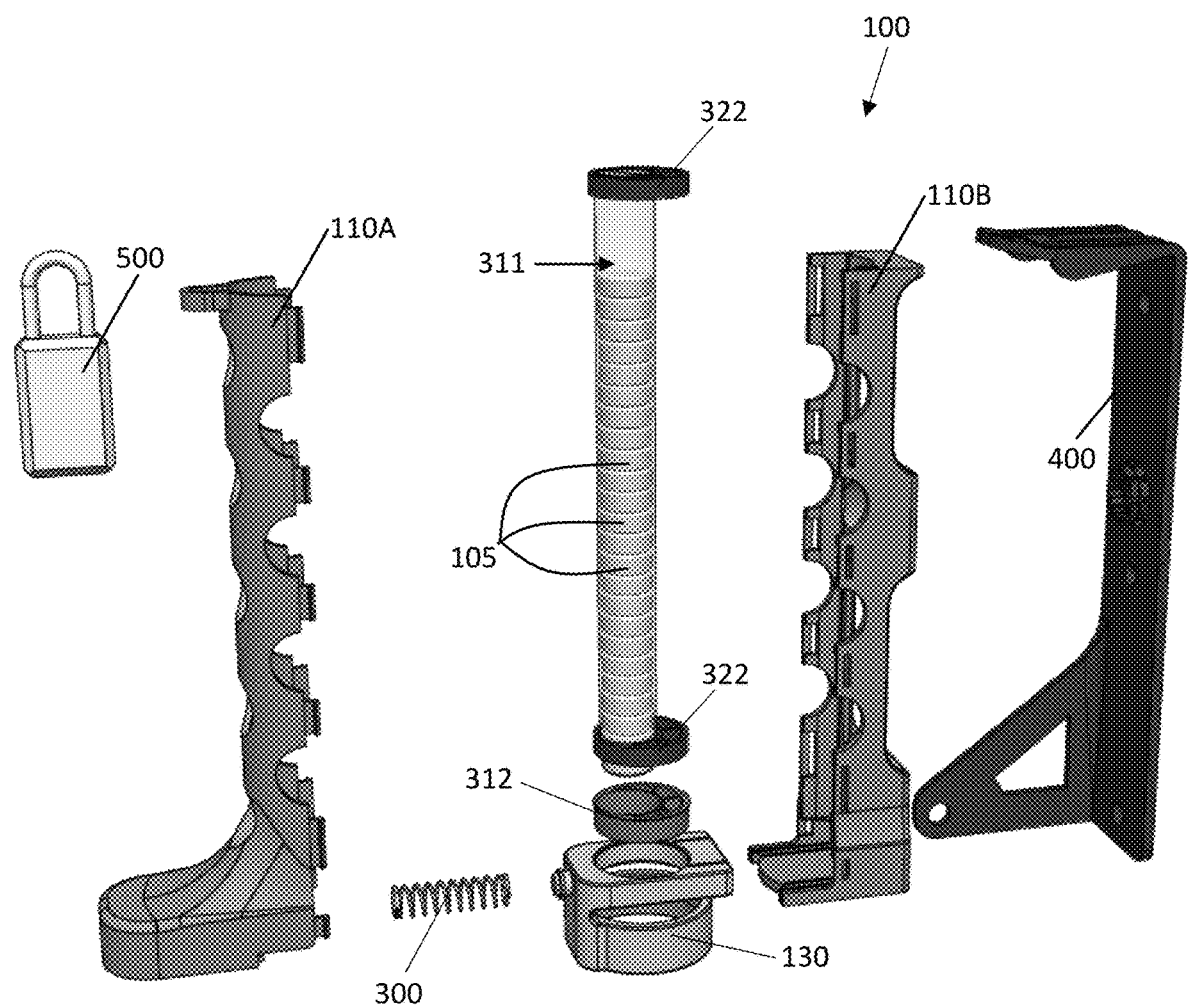
FIG. 10 is an exploded perspective view of an exemplary tablet dispensing system according to another embodiment.

FIGS. 1-10 illustrate various views of an embodiment of a sleeve 110 for a tablet dispensing system 100. In some embodiments, as illustrated in FIGS. 7A and 10, the sleeve 110 includes two parts 110A and 110B that are snapped or otherwise attached together. Manufacturing the sleeve 110 in two parts allows for ease of assembly of the slide 130 (or 330) and the spring 300 within the first part 110A of the sleeve 110 and then attaching the second part 110B of the sleeve 110 onto the first part 110A and over the slide 130 (or 330) and the spring 300.

In an embodiment the sleeve 110 includes a base 120 and a slide 130 as shown in FIGS. 7A, 10, and 14-17, or a slide 330 as shown in FIGS. 20-24. The slide 130, 330 is shown in cross-section assembled to the base 120 in FIGS. 6, 31, and 32. Referring in particular to FIGS. 3-6, 31, and 32, the sleeve 110 defines a first longitudinal axis 140 that is disposed along a center line of a volume 150 defined within at least a portion of the sleeve 110, for example, as defined by at least three sides of the sleeve 110.

In cross-section the sleeve 110 and/or the volume 150 defined by at least a portion of the sleeve 150 can be any shape as desired to match a corresponding shape of tablets 105 to be dispensed, for example, see FIGS. 25-30. In an embodiment, the sleeve 110 defines an internal volume 150 that is generally round in cross-section. In addition, in an embodiment the sleeve 110 does not fully encircle the volume 150 but rather includes an open portion 160. In some embodiments, the sleeve 110 includes the open portion 160, but in other embodiments the sleeve fully encircles the volume 150 and does not have the open portion 160.

Referring to FIGS. 1-6, 31, and 32, in an embodiment the sleeve 110 includes a first opening 170 at a first end 180 and a second opening 190 at a second end 200. In an embodiment, as best seen in FIGS. 4, 6, 31, and 32, the base 120 extends from the second end 200 of the sleeve 110 transversely to the first longitudinal axis 140. In an embodiment a peripheral skirt 210 extends longitudinally from the base 120. As visible in FIGS. 1, 5, and 6, a first barrier 220 is supported by the peripheral skirt 210 at a predetermined distance T from the second opening 190 at the second end 200. The first barrier 220 is attached to the peripheral skirt 210, for example, as an integral part of the peripheral skirt 210, by an adhesive, a melting together of components, or other mechanism for attachment as may be known in the art. In an embodiment the first barrier 220 is removably attached to the peripheral skirt 210.

The first barrier 220 is transverse to the second opening 190 at the predetermined distance T from the second end 200 and intersects with the first longitudinal axis 140 of the sleeve 110. The base 120 includes a portion 230 across which the first barrier 220 does not extend. In the portion 230 transversely aligned shoulders 235 extend from an edge of the first barrier 220 and protrude inwardly from opposite sides of the peripheral skirt 210 at the predetermined distance T from the second end 200. As is explained more fully hereinbelow, the first barrier 220 blocks egress of tablets 105 out of the tablet dispensing system 100 from the internal volume 150 until and unless the slide 130 (or 330) is moved transversely to the axis 140 to assist in dispensing the tablet 105.

A first embodiment of the slide 130 is illustrated in FIGS. 7A, 10, and 14-17. The slide 130 includes a first level (or second barrier) 240 having a first passage 250 disposed therethrough and a second level (or third barrier) 260 having a second passage 270 disposed therethrough. The first and second levels (or second and third barriers) 240, 260 and the first and second passages 250, 270 disposed respectively therethrough can have the same or different cross-sectional shapes, and the same or different transverse dimensions, and can for example, be made to match the shapes and sizes of tablets 105 to be dispensed as illustrated without limitation in FIGS. 25-30. In an embodiment as shown in FIG. 15 the first level is shown having a rounded rectangular cross-sectional shape and the second level 260 is shown to have a circular cross-sectional shape where the first level 240 has a somewhat smaller transverse dimension than that of the second level 260. In other embodiments the first and second levels 240, 260 have other cross-sectional shapes and different relative sizes, without limitation, from those illustrated in FIG. 15.

In an embodiment, a second longitudinal axis 280 is disposed through the geometric center of the first passage 250 and further passes through the second passage 270 so that the first and second passages 250, 270 are aligned in the sense that at least a portion of the first passage 250 overlaps with the second passage 270 when viewed along the second longitudinal axis 280. In another embodiment the second longitudinal axis 280 is disposed through the geometric centers of both the first and second passages 250, 270. In an embodiment both of the first and second passages 250, 270 have circular cross-sections, but in other embodiments both of the first and second passages 250, 270 have other cross-sectional shapes, for example, to match the cross-sectional shape of the volume 150 of the sleeve 110. In another embodiment, the first passage 250 has a different cross-sectional shape than that of the second passage 270. In an embodiment the first passage 250 has a smaller transverse dimension 255 (see FIG. 15) than that of the second passage 270. In other embodiments the first and second passages 250, 270 have the same transverse dimension or the second passage 270 has a larger transverse dimension that that of the first passage 250.

Referring to FIGS. 14, 16, and 17, the first and second levels (or second and third barriers) 240, 260 are separated longitudinally by a riser 290. Referring to FIG. 6, when assembled with the sleeve 110, the slide 130 is disposed with the first level 240 positioned between the first barrier 220 and the second end 200 of the sleeve 110. Or stated another way, the slide 130, 330 is disposed on the base 120 so that the first barrier 220 is positioned between the second and third barriers 240, 260. As can be seen in FIG. 6, the riser 290 is long enough longitudinally to provide enough separation between the first and second levels 240, 260 to accommodate the first barrier 220 therebetween. The slide 130 is biased by a spring 300 toward a first side of the sleeve 110 so that the first barrier 220 blocks at least one of the aligned passages 250, 270. In an embodiment, the slide 130 is biased by the spring 300 so that the first and second longitudinal axes 140, 280 are aligned. The spring 300 is disposed between the peripheral skirt 210 of the base 120 and the slide 130, 330. As noted above, in an embodiment the slider 130 (or 330) and the spring 300 are assembled into the sleeve 110 with the sleeve in two pieces 110A and 110B, which are subsequently snapped or otherwise attached together to contain the slider 130 and the spring 300.

Figures 11A, 11B:
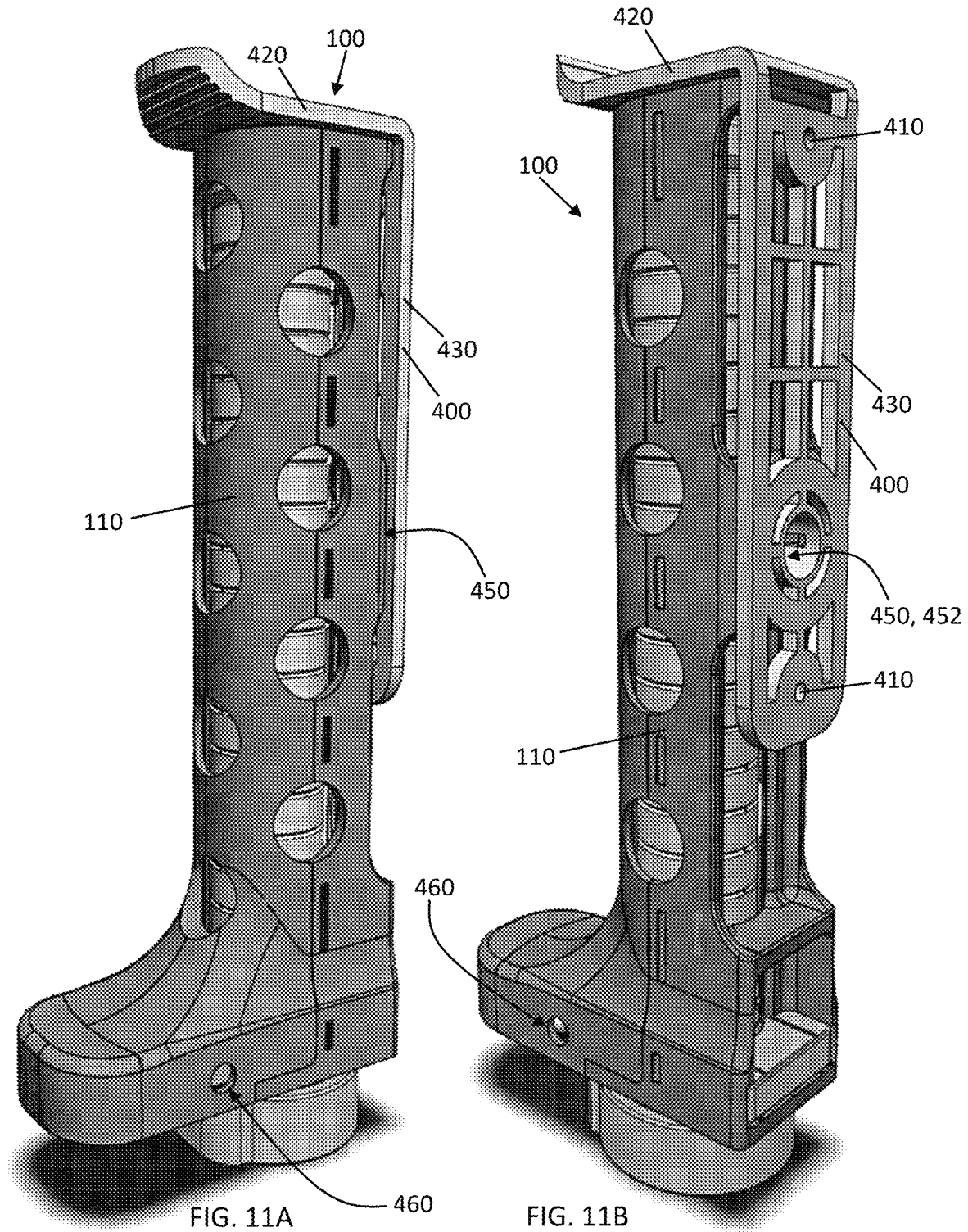
FIG. 11A is a front perspective view of an exemplary dispensing system according to another embodiment.
FIG. 11B is a rear perspective view of the exemplary dispensing system shown in FIG. 10.

Referring to FIGS. 7A-12B, in an embodiment the tablet dispensing system 100 includes a mounting bracket 400 adapted to mount to any vertical surface, for example, via screws or other fasteners disposed through one or more holes 410 disposed through the mounting bracket 400 (see FIG. 11B). Referring to FIGS. 7A-10 in an embodiment the mounting bracket 400 includes a top cover portion 420, a vertical surface attachment portion 430, and at least one transverse gusset 440. FIG. 8 illustrates the mounting bracket 400 having only a single transverse gusset 440; however in other embodiments the transverse gusset 440 extends at least partly over two opposite sides of the sleeve 110. An embodiment of the mounting bracket 400 shown in FIGS. 11A and 11B lacks the at least one transverse gusset 440.

In an embodiment the sleeve 110 includes one or more mounting points 165 that attaches the sleeve 110 to the mounting bracket 400, or alternatively attaches he sleeve 110 directly to a vertical surface. As best seen in FIGS. 1 and 4-6 in an embodiment the one or more mounting points 165 are disposed on an opposite side of the sleeve 110 from the side to which the base 120 transversely extends. In an embodiment the one or more mounting points 165 are manufactured integrally with the sleeve 110; however, in other embodiments the one or more mounting points 165 can be separately manufactured and attached to the sleeve 110, for example without limitation, by an adhesive, a melting together of components, or other mechanism for attachment as may be known in the art. In an embodiment the one or more mounting points 165 are removably attached to the sleeve 110.

In FIGS. 1 and 4-6, two mounting points 165 are shown; however, other embodiments can have one mounting point 165 or three or more mounting points 165 as might be desirable, for example, depending on the shape of or material comprising the vertical surface attachment portion 430 of the mounting bracket 400. In an embodiment an opening 168 (see FIGS. 1, 3, 5, and 6), for example, to accommodate a fastener, is disposed through each mounting point 165.

Referring to FIGS. 7A, 7B, and 9-12, in an embodiment the sleeve 110 includes one or more mounting points 450 that transversely extend from a side of the sleeve 110 opposite from the side to which the base 120 transversely extends. In an embodiment, the one or more mounting points 450 include a circular connector 452 (see FIGS. 11, 31, and 32). The circular connector 452 is adapted to rotatably attach the mounting point 450 to the mounting bracket 400 to allow the sleeve 110 to be rotated relative to the mounting bracket 400. For example, as illustrated in FIGS. 12A and 12B, the sleeve 110 is shown rotated around the mounting point 450 through the arc 465 relative to the mounting bracket 400. Such rotation provides access to the first opening 170 at the first end 180 of the sleeve 110, for example, to allow a tube adapter 310 to be loaded into the sleeve 110 as shown by the arrow 441 as illustrated in FIG. 12B. The circular connector 452 in an embodiment is, for example without limitation, a circular boss that snaps into or through a hole restricting lateral motion between the circular connector 452 and the hole but allowing for relative rotation therebetween. In other embodiments the circular connector 452 is another sort of connector that allows for a rotatable connection between the sleeve 110 and the mounting bracket 400.

Referring to FIGS. 7B, 9, 11A, and 11B, in an embodiment the sleeve 110 includes a mounting point 460 disposed through the peripheral skirt 210. In an embodiment the mounting point 460 comprises one or more holes 460 disposed through the peripheral skirt 210. In an embodiment the one or more holes 460 rotatably attach over at least one pin 462 connected to the mounting bracket 400, for example connected to the at least one transverse gusset 440. For example, referring to FIG. 7B, the sleeve 110 is rotatable relative to the mounting bracket 400 in a direction of the arrow 470 around the mounting point 460 as indicated by the arrow 475.

The at least one pin 462 in an embodiment attaches to the mounting bracket 400, for example without limitation, by a snap fit, a press fit, or by another attachment that allows for a rotatable connection between the mounting bracket 400 and the sleeve 110. In an embodiment having two transverse gussets 440 (not shown), the sleeve 110 includes a pair of holes 460 disposed through opposite sides of the peripheral skirt 210, wherein the pair of holes 460 rotatably attach over a pair of pins 462 connected to the mounting bracket 400.

In the embodiment of the sleeve 110 having the open portion 160 the mounting points 165 span the open portion 160. In other embodiments (not shown) where the sleeve 110 fully encircles the volume 150 and does not have the open portion 160, the mounting points 165 can be positioned in the same positions as those spanning the open portion 160. In this embodiment lacking the open portion 160, the openings 168 are disposed through the mounting point 165 and a portion of the sleeve 110 adjacent to each mounting point 165.

In one embodiment the sleeve 110 includes holes 175 disposed therethrough along a length thereof. The holes 175 can be distributed along one or more sides of the sleeve 110, for example, along three sides of the sleeve 110 as shown in FIGS. 1-12 to allow an observer to view the fill level of the internal volume 150 of the sleeve 110. The holes 175 can be circular as shown or have any shape as desired for aesthetic or other purposes. The holes 175 can number four or five as shown, in FIGS. 7-12, more than five as shown in FIGS. 1-6, or the sleeve 110 can include any other number of holes 175 less than, equal to, or greater than five as desired.

In an embodiment the sleeve 110 can be locked relative to the mounting bracket 400 to prevent movement or rotation of the sleeve 110 relative to the mounting bracket 400. For example, in an embodiment as best shown in FIGS. 7B-9 and 13B, the sleeve 110 comprises a loop of material 480 extending from the sleeve 110. The mounting bracket 400 also includes a loop of material 490. The loop of material 480 extending from the sleeve 110 is adapted to align with the loop of material 490 on the mounting bracket 400 to allow the sleeve 110 to be locked in place relative to the mounting bracket 400, for example by the lock 500 illustrated in FIGS. 7B, 9, and 13B. Referring for example to FIG. 7B, the lock 500 disposed through the loops 480, 490 prevents the sleeve 110 from moving relative to the mounting bracket 400, whether that motion is rotational around the mounting point 450 or rotational around the mounting point 460.

Figure 13A:
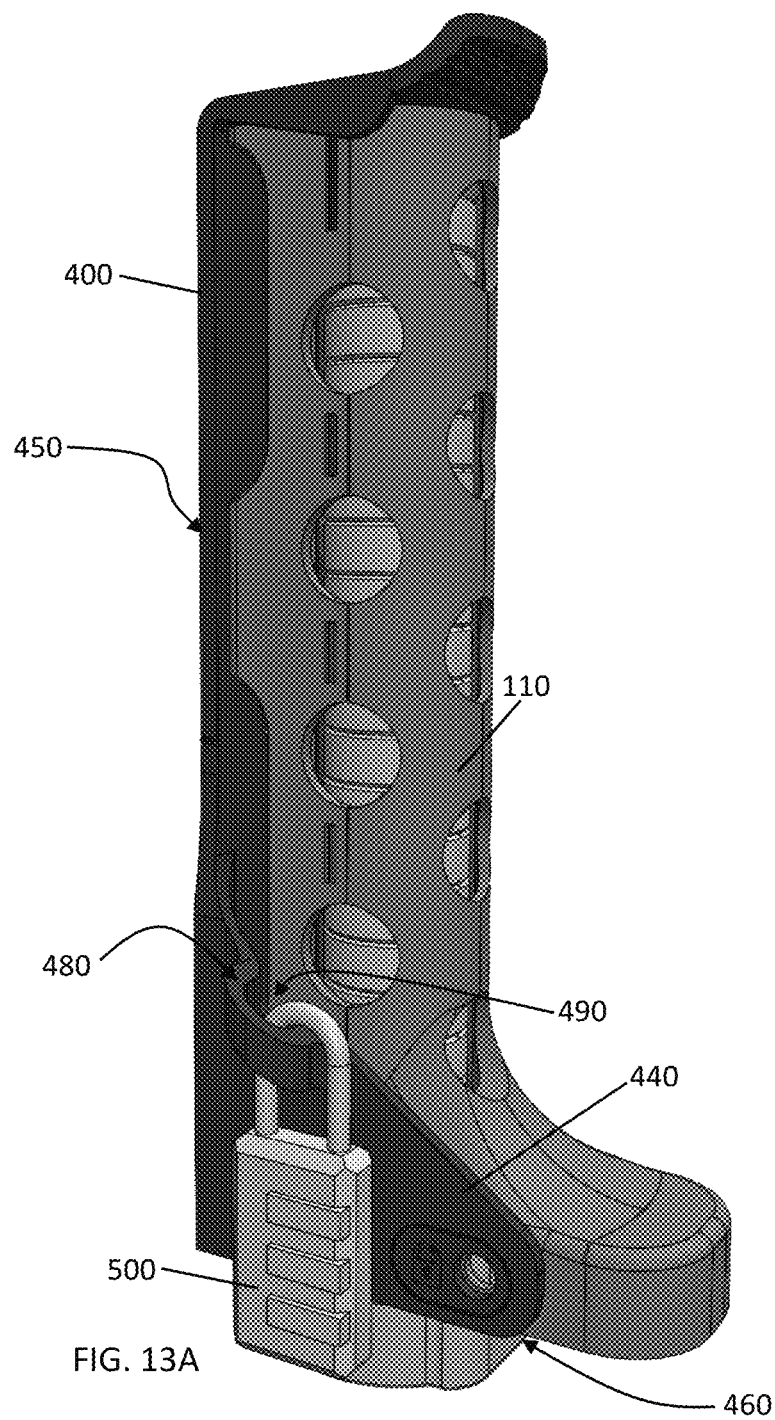
FIG. 13A is a front perspective view of an exemplary dispensing system according to a further embodiment.
Figure 13B:
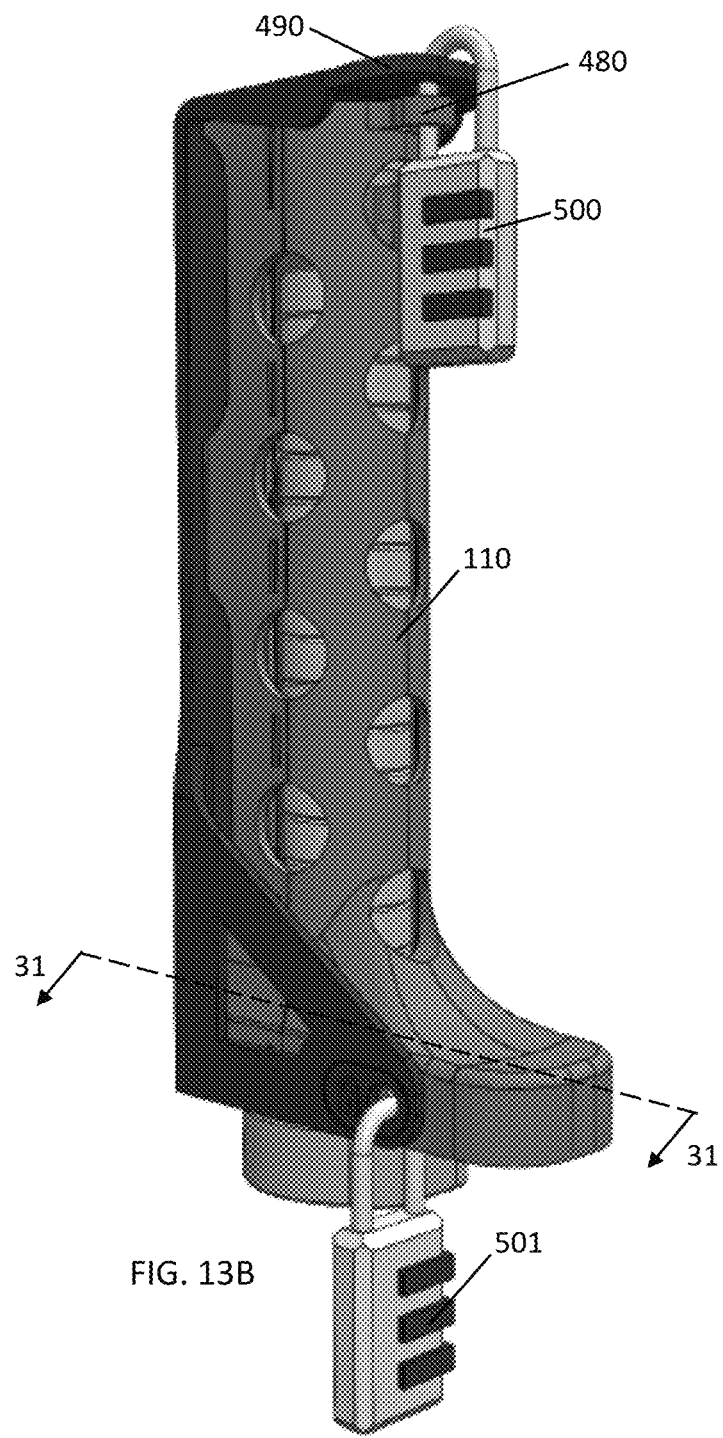
FIG. 13B is a front perspective view of an exemplary dispensing system according to a yet another embodiment.

In an embodiment the loops of material 480, 490 extend from a top portion of the sleeve 110 and the mounting bracket 400 as shown in FIGS. 7B, 9, and 13B. In other embodiments, the loops of material 480, 490 extend from a different portion of the sleeve 110 and the mounting bracket 400, for example without limitation on or near the transverse gusset 440, as shown in FIG. 13A.

Figure 7A:
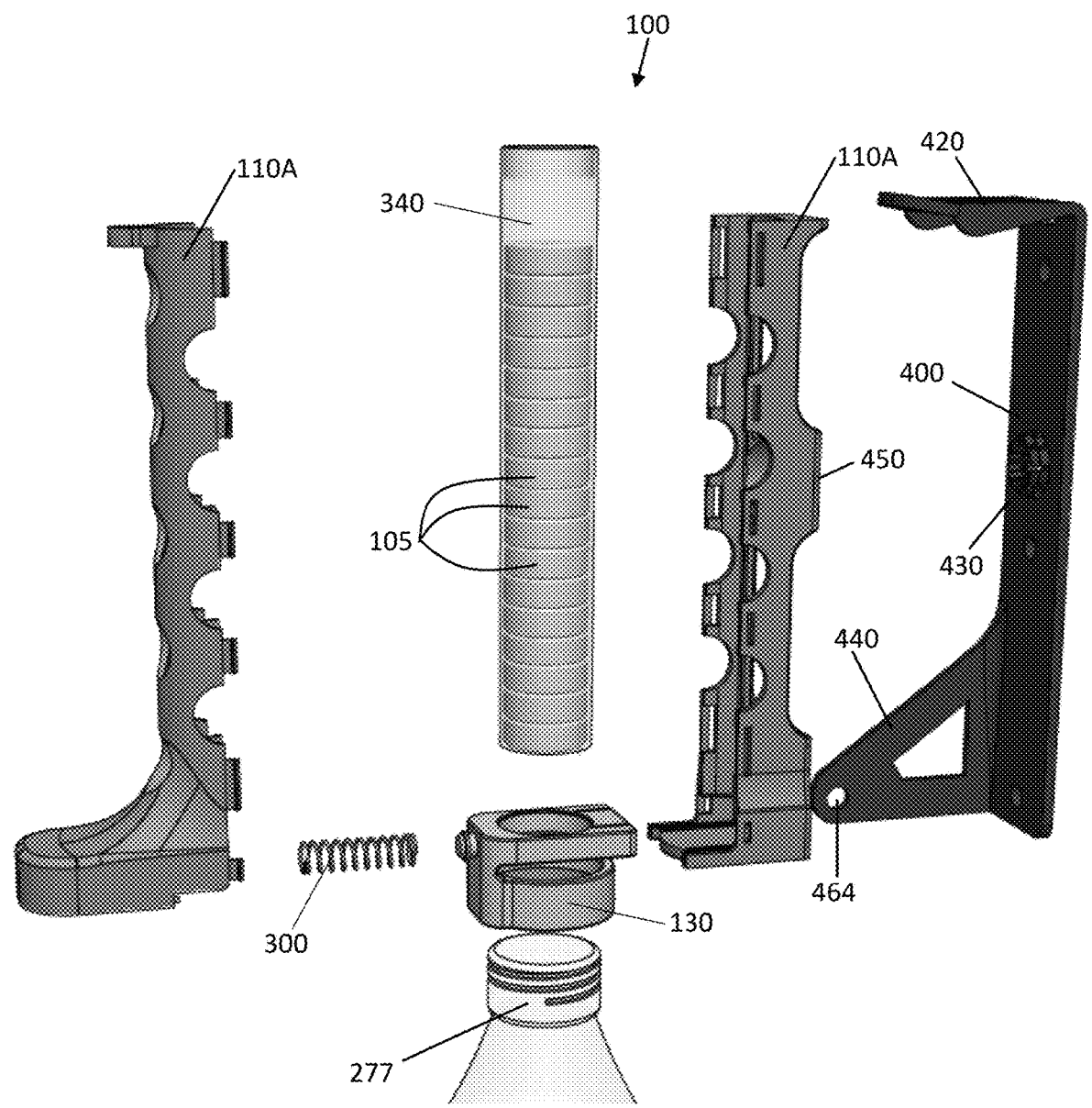
FIG. 7A is an exploded perspective view of an exemplary tablet dispensing system according to an embodiment.
Figure 12A:
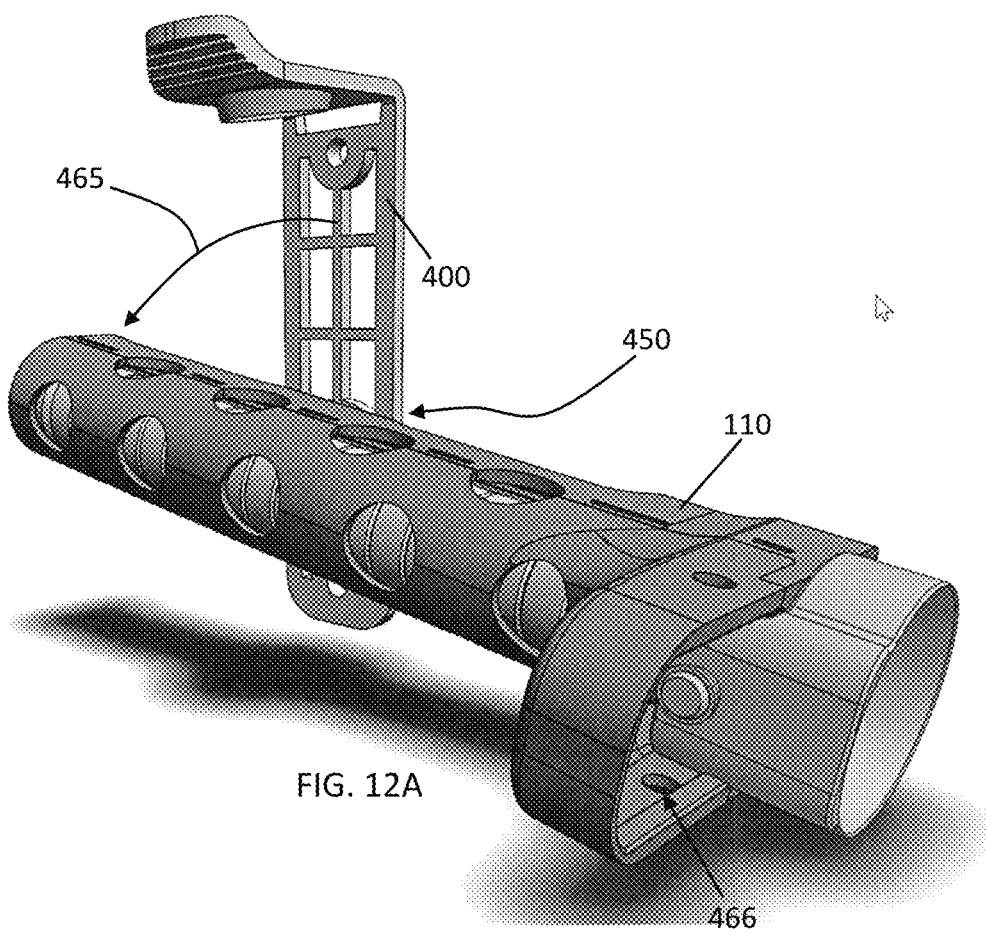
FIG. 12A is a front perspective view of an exemplary dispensing system with the sleeve rotated relative to a mounting bracket according to an embodiment.
Figure 12B:
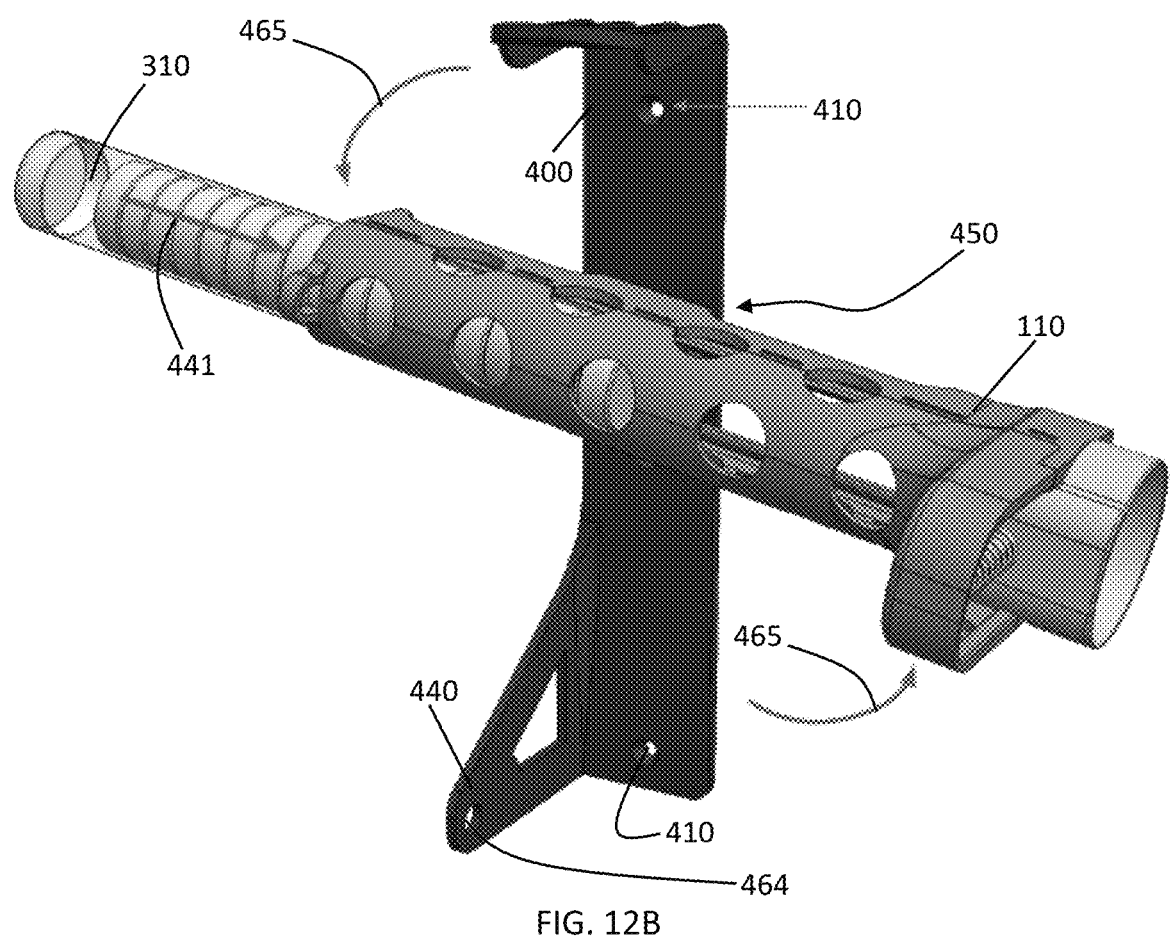
FIG. 12B is a front perspective view of an exemplary dispensing system with the sleeve rotated relative to a mounting bracket according to another embodiment.

In another embodiment, as shown in FIG. 13B, the sleeve 110 can be locked against relative rotation with the mounting bracket 400, and also locked to the gusset 440 to prevent tablets 105 from being dispensed. As is explained fully hereinbelow, tablets 105 are dispensed when the slide 130, 330 is pulled forward relative to the sleeve 110. Referring, for example, to FIGS. 7A and 12B, in an embodiment the bracket 400 includes a hole 464 disposed through the gusset 440. When the sleeve 110 is disposed upright on the mounting bracket 400, the hole 464 aligns with a hole 466 (see, e.g., FIGS. 1 and 12A), disposed through the peripheral skirt 210 at the portion 230 of the base 220 across which the first barrier 220 does not extend. A body, for example, a lock latch disposed through the aligned holes 464 and 466 effectively blocks the sleeve 130 (or 330) from being translated to the dispensing position (see FIG. 32 below). Thus, the lock 501 illustrated in FIG. 13B prevents tablets 105 from being dispensed.

Referring again to FIG. 6, the slide 130, 330 is biased by the spring 300, which is held between a first protrusion 360 disposed on the peripheral skirt 210 and a second protrusion 370 disposed on the slide 130, 330. In an embodiment, the spring 300 is held between the first and second protrusions 360, 370 by the force of its own compression. In other embodiments the spring 300 is securely attached at both ends to the first and second protrusions 360, 370, for example, by snapping into a groove, by adhesive, or by other methods of attachment of a spring to a protrusion as may be known in the art. Pushing the slide 130, 330 transversely against the bias of the spring 300 allows at least a portion of the first passage 250 to move transversely beyond an edge of the first barrier 220.

Still referring to FIG. 6, as noted hereinabove, the base 120 includes a portion 230 across which the first barrier 220 does not extend. In the portion 230 transversely aligned shoulders 235 extend from an edge of the first barrier 220 and protrude inwardly from opposite sides of the peripheral skirt 210 at the predetermined distance T from the second end 200. The slide 130, 330 travels transversely against the bias of the spring 300 supported by the first barrier 220 and the transversely aligned shoulders 235 extending inwardly from opposite sides of the peripheral skirt 210 and at the predetermined distance T from the second end 200.

An embodiment of a first tube adapter 310, 311, for example, as shown in FIGS. 18A and 18B, can be disposed within the volume 150. The first tube adapter 310, 311 is sized to fit within the sleeve 110 in one of multiple embodiments. In a first embodiment the first tube adapter 310 fits within the sleeve 110 by having ribs 320 (see FIG. 18A) that extend transversely along the length of the first tube adapter 310. The ribs 320 are sized to engage with the interior surface of the sleeve 110 to keep the first tube adapter 310 generally centered therein. Three ribs 320 are shown; however, there can be four, five, six, or more ribs 320 as desired on the first tube adapter 310. The first tube adapter 310 is designed for use directly with the slide 330.

In a second embodiment the first tube adapter 311 lacks the ribs 320, but as shown in FIGS. 10 and 35, the first tube adapter 311 lacking the ribs 320 engages with small tube adapter rings 322 that support the first tube adapter 311 proximate to its top and bottom ends within the sleeve 110. An interior of the first tube adapter 310, 311 has a first transverse dimension 325 and is configured to hold tablets 105 stacked longitudinally within. In an embodiment, the tube adapter rings 322 attach to the first tube adapter 311 via a press fit; however, in other embodiments the tube adapter rings 322 attach to the first tube adapter 311 via a snap mechanism or an adhesive, or via any other suitable mechanism for attachment as is known in the art.

In an embodiment utilizing the first tube adapter 311 for use with the slide 130, a slide adapter 312 is disposed within the first passage 250 as shown in FIGS. 10 and 35. The slide adapter 312 is sized to fit within the first passage and be supported by the first barrier 240 while also supporting the first tube adapter 311. Alternatively, in another embodiment the first tube adapter 310 can be used directly with the slide 330.

The first transverse dimension 325 can be sized larger or smaller limited only by the transverse dimension of the interior volume 150 and a sidewall thickness of the first tube adapter 310, 311. In other words, any number of tube adapters in addition to any described herein can be made to accommodate tablets 105 of any size limited only by the maximum size of the sleeve 110.

For example, an embodiment of a second tube adapter 340 is shown in FIGS. 19A, 19B, and 34. The second tube adapter 340 is sized to fit within the interior volume 150 and be centered therein without the need for the ribs 320 or the tube adapter rings 322. The second tube adapter 340 is configured to hold tablets 105 stacked longitudinally within. The second transverse dimension 345 of the second tube adapter is larger than the first transverse dimension 325 of the first tube adapter 310, 311.

Referring to FIG. 33, the tube adapter 310, 311, 340, whether it is the first tube adapter 310, 311 or the second tube adapter 340, or any subsequent or additional tube adapter, in an embodiment includes a top insert plug 342 disposed within a first or top end and a bottom insert plug 343 disposed within a second or bottom end. In an embodiment the bottom insert plug 342 is shaped and sized similar to a tablet 105. In operation the top insert plug 342 includes a seal with the tube adapter 310, 311, 340 and is never removed therefrom. Rather upon insertion of the tube adapter 310, 311, 340 into the sleeve 110, the top insert plug 342 is pushed into the tube adapter 310, 311, 340 so that the bottom plug 343 is pushed out the bottom of the tube adapter 310, 311, 340 while the top of the tube adapter 310, 311, 340 remains closed and sealed.

Referring back to FIG. 15, a transverse dimension 255 of the first passage 250 is at least as large as the first transverse dimension 345 of the second tube adapter 340. Referring to FIGS. 14, 16, and 17, a longitudinal thickness of the first level 240 is less than or equal to a longitudinal thickness of a tablet 105, indicated as TL in FIGS. 25 and 26. The geometries of the slide 130 and the tube adapters 310, 311, 340 are discussed further hereinbelow in explaining the operation of the tablet dispensing system 100.

Tablets 105 for use with the tablet dispensing system 100 can also have a variety of shapes and sizes to generally match the cross-sectional shape of the tube adapters 310, 311, 340 and the slides 130, 330. For example, referring to FIGS. 25-30, a series of tablets 105 of different shapes are illustrated. FIG. 25 illustrates a tablet 105 with a round shape in plan view having a tablet transverse dimension D as shown and a tablet longitudinal thickness TL as shown. FIG. 26 illustrates a tablet 105 with a square shape in plan view having a tablet transverse dimension D as shown and a tablet longitudinal thickness TL as shown. FIGS. 27-30 illustrate tablets 105 having other shapes in plan view, for example, triangular, elliptical, pentagonal, and hexagonal. There is no limitation on the shape of the tablets 105 that can be used with the dispensing system 100, or the tube adapters 310, 311, 340, or of the first passages 250, 350 disposed respectively through the slides 130, 330.

Figure 20:
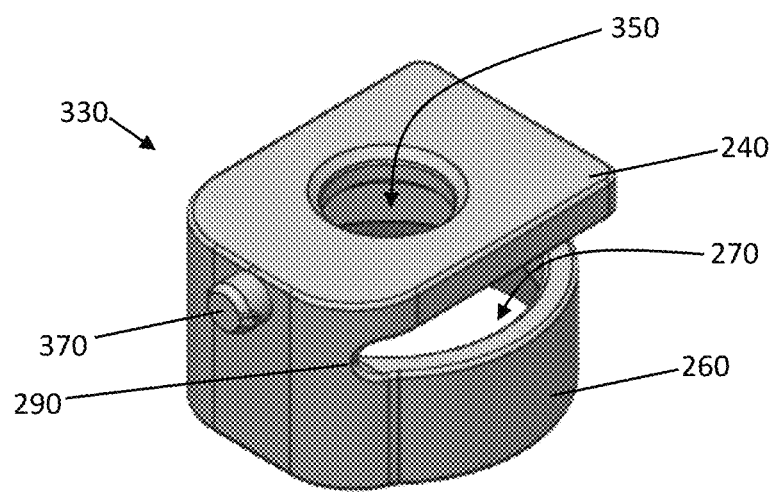
FIG. 20 is a front perspective view of a second embodiment of a slide.
Figure 21:
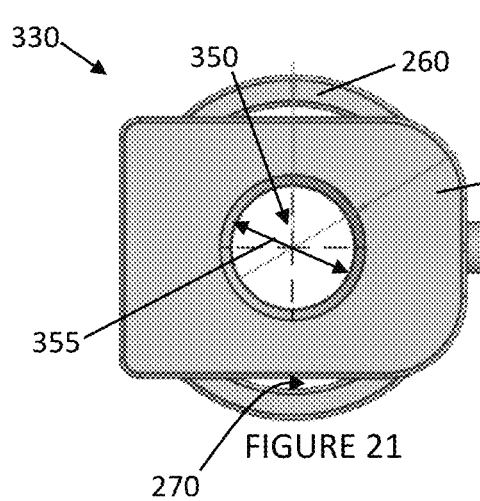
FIG. 21 is a top plan view of the slide shown in FIG. 20.

A second embodiment of the slide 330 is illustrated in FIGS. 20-24. The slide 330 is similar to the slide 130 except that a first passage 350 disposed through the first level 240 as shown in FIGS. 20 and 21 has a smaller transverse dimension 355 (see FIG. 21) than the transverse dimension 255 of the first passage 250 shown in FIGS. 14 and 15. The slide 330 is otherwise identical to the slide 130. The transverse dimension 355 of the first passage 350 is at least as large as the first transverse dimension 325 of the first tube adapter 310. The first and second passages 350, 270 respectively of the second embodiment of the slide 330 can have the same or different cross-sectional shapes, and the same or different transverse dimensions, and can for example, be made to match the shapes and sizes of tablets to be dispensed as illustrated without limitation in FIGS. 25-30. Although the tablet dispensing system 100 having the slide 130 could be used with tablets having a smaller lateral dimension than the transverse dimension 255 of the first passage 250, providing an embodiment of the slide 330 having a transverse dimension 355 of the first passage 350 and a first tube adapter 310 allows for dispensing of smaller tablets without any additional motion or space between the tablets and the first passage 350.

Referring to FIGS. 1, 5, and 6, in one embodiment the first barrier 220 is removably attached to the peripheral skirt 210. Removal of the first barrier 220 allows a first embodiment of the slide 130, 330, for example the slide 130, to be removed and replaced with a second embodiment of the slide 130, 330, for example the slide 330. Changing out the slide 130, 330 can be useful to match the size of the transverse dimension 255, 355 of the first passage 250, 350 to the first transverse dimension 325, 345 of the first and second tube adapters 310, 340, respectively. Of course, having the slide adapter 312, or multiple different sized slide adapters 312 allows for the use of any number of multiple different tube adapters 311 and others for dispensing tablets of any desired transverse dimensions simply by changing the tube adapter 311 and others and the slide adapter 322 as needed to fit the tablets 105.

Figure 24:
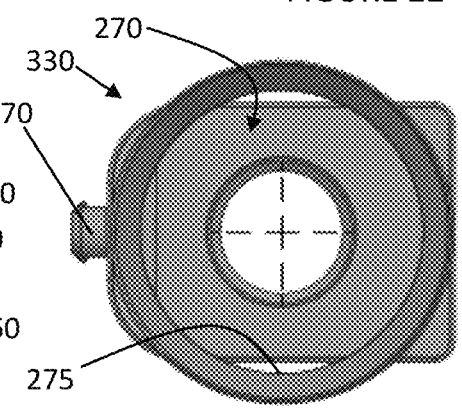
FIG. 24 is a bottom plan view of the slide shown in FIG. 20.

Referring to FIG. 24 in an embodiment an internal surface 275 of the second passage 270 (of either slide 130, 330) is threaded. Threads disposed on the internal surface 275 enable a threaded container 277 (see FIGS. 7A and 32) to be engaged with the slide 130, 330 so that a tablet dispensed from the tablet dispensing system 100 falls directly into the container 277.

Referring again to FIGS. 6, 31, and 32, operation of an embodiment of the tablet dispensing system 100 is described hereinbelow. The tablet dispensing system 100 in an embodiment is oriented with the first longitudinal axis 140 aligned vertically with the first end 180 disposed above the second end 200. Tablets 105 are supplied stacked longitudinally within a tube adapter 310, 311, 340 or other sized adapter selected to match the transverse size of the tablets. The tube adapter 310, 311, 340 holding the tablets stacked longitudinally therein is introduced into the first opening 170 so that a bottom end of the tube adapter 310, 311, 340 is supported by the first transversely extending barrier 240. The top insert plug 342 is pushed down into the tube adapter 310, 311, 340 so that the bottom insert plug 343 is pushed out the bottom of the tube adapter 310, 311 and into the first passage 250, 350 disposed through the first level (or the second barrier) 240.

The slide 130, 330 is pushed transversely against the bias of the spring 300 so that at least a portion of at least one of the first and second passages 250, 270, for example the first passage 250 disposed through the first level (or the second barrier) 240, moves transversely beyond an edge of the first barrier 220 thereby allowing the bottom insert plug 343 to drop through the first passage 250 and the second passage 270. When the bottom insert plug drops out of the second passage 270, the bottommost tablet 105 drops into the first passage 250. At this point the tablet dispensing system 100 is ready to dispense tablets 105.

Referring to FIGS. 31 and 32, the tablet dispensing system 100 is illustrated in a non-dispensing state in FIG. 31 and in an actuated or dispensing state in FIG. 32. The system 100 operates the same regardless of the tube adapter 310, 311, 340, the slide 130, 330, or the size and/or shape of the tablets 105. To dispense the first and every subsequent tablet 105, the slide 130 is pushed transversely against the bias of the spring 300 as shown in FIG. 32 so that at least a portion of at least one of the first and second passages 250, 270, for example the first passage 250 disposed through the first level (or the second barrier) 240, moves transversely beyond an edge of the first barrier 220 thereby allowing the next tablet 105 at the bottom of the stack to drop through the first passage 250 and the second passage 270 as shown by the arrow 295.

The slide 130, 330 travels transversely against the bias of the spring 300 supported in part by the first barrier 220 and also supported by the transversely aligned shoulders 235 extending inwardly from opposite sides of the peripheral skirt 210 at a predetermined distance T from the second end 200. In an embodiment of the tablet dispensing system 100, an additional step in the operation of the tablet dispensing system 100 is mounting the tablet dispensing system 100 to a vertical surface via the mounting bracket 400 before introducing the first tube adapter 310, 311, 340.

Figure 22:
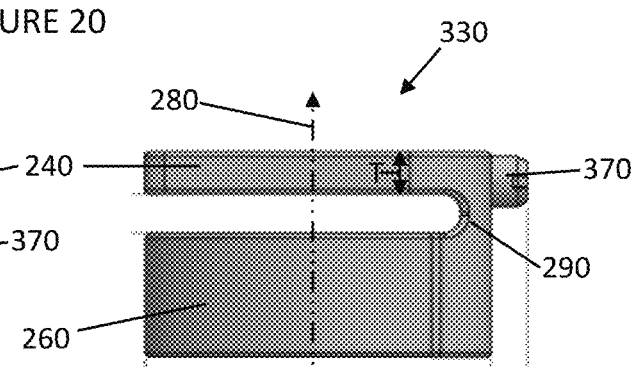
FIG. 22 is a right side view of the slide shown in FIG. 20.
Figure 23:
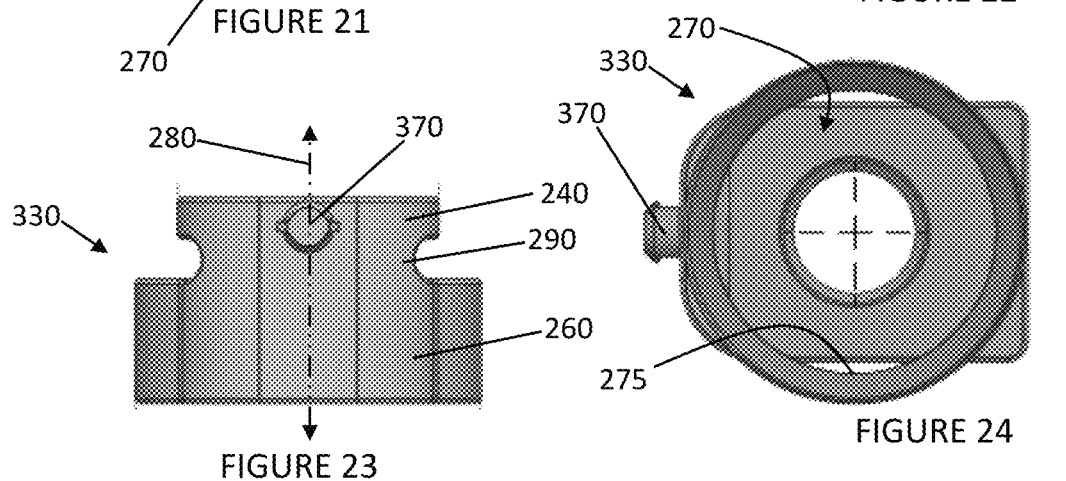
FIG. 23 is a front elevational view of the slide shown in FIG. 20.

Referring to FIGS. 6, 16, and 22, for the above described dispensing operation to operate smoothly requires that a longitudinal thickness T of the first level (or the second barrier) 240 of the slide 130, 330 be less than or equal to a longitudinal thickness of a tablet 105. This size relationship allows one tablet 105 at a time to be drawn transversely off the bottom of a stack of tablets by the slide 130, 330. If the longitudinal thickness T of the first level 240 were greater than the longitudinal thickness of a tablet 105 the first passage 250 would surround a portion of a second tablet 105 stacked on top of the bottom tablet. If a second tablet 105 were so surrounded then a transverse motion of the slide 130, 330 would pull the second tablet 105 into contact with a surface of the internal volume 150, which would effectively jam the slide 130, 330 from moving further transversely and effectively defeat the dispensing of the bottom tablet 105. Providing that the longitudinal thickness T of the first level 240 is less than or equal to the longitudinal thickness of a tablet 105 therefore ensures that the bottom tablet 105 is smoothly dispensed from the tablet dispensing system 100. It should be further noted that in an embodiment the bottom insert plug 343 has the same longitudinal thickness of a tablet 105, thereby allowing the bottom insert plug 343 to be dispensed in the same way but before any actual tablets 105 are dispensed.

It should be noted embodiments utilizing tube adapters 310, 311, 340 are disclosed herein; however, a tube adapter of any sort is not required. It should be noted that the steps in dispensing a tablet do not require the presence of any sort of adapter tube 310, 311 340. In an embodiment, individual tablets 105 can be loaded directly into the sleeve 110 for dispensing one at a time without any type of tube adapter.

Those skilled in the art will appreciate that the invention described herein is susceptible to variations and modifications other than those specifically described, and that each embodiment is also provided with features that may be applicable to other embodiments. It is to be understood that the invention includes all such variations and modifications that fall within its spirit and scope. The invention also includes all the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

INDUSTRIAL APPLICABILITY

A tablet dispensing system is disclosed herein for dispensing disinfectant tablets one at a time without being touched directly into a bottle or container. The tablet dispensing system can be mounted on a wall and locked in place and also locked against use once loaded with tablets to prevent unauthorized use, tampering with, or theft of the tablets. The tablet dispensing system can accommodate tablets of differing sizes with a simple change in components. The tablet dispensing system can be manufactured in industry for use anywhere disinfectant solutions are used.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

I claim:

1. A tablet dispensing system, comprising
   a sleeve comprising a wall that defines an inner volume having a first longitudinal axis disposed through the inner volume, wherein the sleeve further comprises a first opening at a first end of the sleeve and a second opening at a second end of the sleeve, wherein the first and second openings are disposed on the first longitudinal axis;
   a base extending transversely from the wall at the second end to an endpoint spaced from the wall;
   a peripheral skirt extending longitudinally from the base and beyond the second end;
   a transversely extending first barrier supported by the peripheral skirt at a predetermined distance from the second end and intersecting with the first longitudinal axis of the sleeve;
   a slide having a second longitudinal axis, a transversely extending first level having a thickness measured along the second longitudinal axis, a first passage disposed along the second longitudinal axis therethrough, and a transversely extending second level having a second passage disposed along the second longitudinal axis therethrough, wherein the first and second levels are separated longitudinally by a riser; and
   a spring; wherein
   the slide is disposed with the first level disposed entirely between the first barrier and the second end, and transversely biased by the spring so that the first and second longitudinal axes are aligned, wherein the spring is disposed between the peripheral skirt and the slide; further comprising
   a first tube adapter sized to fit within the sleeve and configured to hold tablets stacked longitudinally within the first tube adapter and having a first tablet transverse dimension;
   wherein a transverse dimension of the first passage is at least as large as the first tablet transverse dimension and the thickness of the first level is adapted to be less than or equal to a longitudinal thickness of a tablet; and further comprising the steps of:
   wherein the first tube adapter includes a first insert plug disposed in a first end and a second insert plug disposed in a second end with tablets stacked longitudinally within the first tube adapter between the first and second insert plugs;

introducing the first tube adapter into the first opening so that the second end of the first tube adapter is supported by the first level;

orienting the tablet dispensing system with the first longitudinal axis aligned vertically and the first end above the second end;

pushing downwardly on the first insert plug, whereby pushing downwardly on the first insert plug pushes the second insert plug out of the second end of the tube adapter and into the first passage;

pushing the slide transversely against the bias of the spring so that at least a portion of the first passage moves transversely beyond an edge of the first barrier thereby allowing the second insert plug to drop through the first passage and the second passage, wherein after the second insert plug drops through the second passage, releasing the slide allowing it to return to a transversely biased position so that a bottommost tablet drops into the first passage; and pushing the slide transversely against the bias of the spring so that at least a portion of the first passage moves transversely beyond an edge of the first barrier thereby allowing the bottommost tablet to drop through the first passage and the second passage.

2. The tablet dispensing system of claim 1, further comprising a mounting bracket adapted to mount to any vertical surface, wherein the sleeve further comprises a mounting point that attaches the sleeve to the mounting bracket.

3. The tablet dispensing system of claim 2, wherein the mounting point is selected from the group of mounting points consisting of a first mounting point that transversely extends from a side of the sleeve opposite from the side to which the base transversely extends, wherein the first mounting point includes a circular connector, whereby the circular connector is adapted to rotatably attach the first mounting point to the mounting bracket, and a second mounting point comprising one or more holes disposed through the peripheral skirt, whereby the one or more holes rotatably attach over at least one pin connected to the mounting bracket.

4. The tablet dispensing system of claim 3, further comprising a first loop of material extending from the sleeve and a second loop of material extending from the mounting bracket, wherein the first loop of material is adapted to align with the second loop of material to allow the sleeve to be locked in place relative to the mounting bracket.

5. The tablet dispensing system of claim 1, wherein pushing the slide transversely against the bias of the spring allows at least a portion of the first passage to move transversely beyond an edge of the first barrier.

6. The tablet dispensing system of claim 5, further comprising shoulders protruding inwardly from internally facing opposite surfaces of the peripheral skirt, the shoulders extending from the edge of the first barrier along the internally facing opposite surfaces and disposed at the predetermined distance from the second end, wherein the slide travels transversely against the bias of the spring supported by the first barrier and the shoulders.

7. The tablet dispensing system of claim 1, further comprising a second tube adapter sized to fit within the sleeve and configured to hold tablets stacked longitudinally within the second tube adapter and having a second tablet transverse dimension.

8. The tablet dispensing system of claim 7, wherein the transverse dimension of the first passage is at least as large as the second tablet transverse dimension and the thickness of the first level is adapted to less than or equal to a longitudinal thickness of a tablet.

9. The tablet dispensing system of claim 1, wherein the spring is held between a first protrusion on the peripheral skirt and a second protrusion on the slide.

10. The tablet dispensing system of claim 1, wherein an internal surface of the second passage is threaded.

11. A tablet dispensing system, comprising:
a sleeve comprising a wall that defines an inner volume having a first longitudinal axis disposed through the inner volume, wherein the sleeve further comprises a first opening at a first end of the sleeve and a second opening at a second end of the sleeve, wherein the first and second openings are disposed on the first longitudinal axis;

a base attached to the second end and extending transversely in a first direction from the wall to an endpoint spaced from the wall, the base supporting a transversely extending first barrier intersecting the first longitudinal axis and disposed transversely to and a predetermined distance from the second opening;

a first slide having second and third barriers separated by a first riser, wherein the second and third barriers include aligned first and second passages, respectively, disposed therethrough; wherein the first slide is disposed so that the first barrier is positioned between the second and third barriers and the first slide so disposed is biased by a spring in a second direction opposite the first direction so that the first barrier blocks at least one of the aligned first and second passages, where the spring is disposed between the base and the first slide; further comprising a first tube adapter sized to fit within the sleeve and configured to hold a first stack of tablets having a first tablet transverse dimension measured transverse to the stack;

one or more second tube adapters configured to each hold a stack of tablets having a tablet transverse dimension measured transverse to the stack;

two or more tube adapter rings attached to each of the one or more second tube adapters, the two or more tube adapter rings sized to fit within the sleeve and stabilize each of the one or more second tube adapters therein; and one or more slide adapters, each disposed within the first passage and supported by the second barrier, and each supporting one of the one or more second tube adapters.

12. The tablet dispensing system of claim 11, wherein pushing the first slide against the bias of the spring allows at least a portion of at least one of the aligned first and second passages to move beyond an edge of the first barrier.

13. The tablet dispensing system of claim 11, wherein a first dimension measured across the first passage is at least as large as the first tablet transverse dimension and wherein the second barrier is adapted to have a longitudinal thickness that is less than or equal to a longitudinal thickness of a tablet of the first stack of tablets.

14. The tablet dispensing system of claim 11, wherein each of the one or more second tube adapters includes a first insert plug disposed in a first end and a second insert plug disposed in a second end with the stack of tablets stacked longitudinally therein between the first and second insert plugs.

15. A method for dispensing tablets, comprising: a sleeve comprising a wall that defines an inner volume having a first longitudinal axis disposed through the inner volume, wherein the sleeve further comprises a first opening at a first end of the sleeve and a second opening at a second end of the sleeve, wherein the first and second openings are disposed on the first longitudinal axis; a base attached to the second end and extending transversely in a first direction from the wall to an endpoint spaced from the wall, the base supporting a transversely extending first barrier intersecting the first longitudinal axis and disposed transversely to and a predetermined distance from the second opening; a first slide having second and third barriers separated by a first riser, wherein the second and third barriers include aligned first and second passages, respectively, disposed therethrough; wherein the first slide is disposed so that the first barrier is positioned between the second and third barriers and the first slide so disposed is biased by a spring in a second direction opposite the first direction so that the first barrier blocks at least one of the aligned first and second passages, where the spring is disposed between the base and the first slide; further comprising a first tube adapter sized to fit within the sleeve and configured to hold a first stack of tablets having a first tablet transverse dimension measured transverse to the stack, one or more second tube adapters configured to each hold a stack of tablets having a tablet transverse dimension measured transverse to the stack; two or more tube adapter rings attached to each of the one or more second tube adapters, the two or more tube adapter rings sized to fit within the sleeve and stabilize each of the one or more second tube adapters therein; and one or more slide adapters, each disposed within the first passage and supported by the second barrier, and each supporting one of the one or more second tube adapters; wherein each of the one or more second tube adapters includes a first insert plug disposed in a first end and a second insert plug disposed in a second end with the stack of tablets stacked longitudinally therein between the first and second insert plugs, and further; including the steps of:

introducing a selected tube adapter of the first or the one or more second tube adapters into the first opening so that the second end of the selected tube adapter is supported by the second barrier;

orienting the tablet dispensing system with the first end above the second end;

pushing downwardly on the first insert plug, whereby pushing downwardly on the first insert plug pushes the second insert plug out of the second end of the selected tube adapter and into the first passage;

pushing the slide transversely against the bias of the spring so that at least a portion of the first passage moves transversely beyond an edge of the first barrier thereby allowing the second insert plug to drop through the first passage and the second passage, wherein after the second insert plug drops through the second passage, releasing the slide allowing it to return to a transversely biased position so that a bottommost tablet of the stack of tablets drops into the first passage; and pushing the slide transversely against the bias of the spring so that at least a portion of the first passage moves transversely beyond an edge of the first barrier thereby allowing the bottommost tablet to drop through the first passage and the second passage.

\* \* \* \* \*